United States Patent
Suttin et al.

(10) Patent No.: US 7,850,452 B2
(45) Date of Patent: Dec. 14, 2010

(54) PRE-STRESSED IMPLANT COMPONENT AND ASSEMBLY

(75) Inventors: Zachary B. Suttin, Palm Beach Gardens, FL (US); James N. Kenealy, III, Hobe Sound, FL (US)

(73) Assignee: Biomet 3i, LLC, Palm Beach Gardens, FL (US)

( * ) Notice: Subject to any disclaimer, the term of this patent is extended or adjusted under 35 U.S.C. 154(b) by 464 days.

(21) Appl. No.: 11/115,654

(22) Filed: Apr. 27, 2005

(65) Prior Publication Data

US 2006/0246396 A1    Nov. 2, 2006

(51) Int. Cl.
*A61C 8/00*    (2006.01)
(52) U.S. Cl. .................................. 433/174; 433/173
(58) Field of Classification Search ................ 433/169, 433/173, 174
See application file for complete search history.

(56) References Cited

U.S. PATENT DOCUMENTS

| | | | |
|---|---|---|---|
| 1,126,219 A | 1/1915 | Hupp | |
| 3,435,526 A | 4/1969 | Brancato | |
| 3,590,485 A | 7/1971 | Chercheve | |
| 3,726,011 A | 4/1973 | Savignano | |
| 3,797,113 A | 3/1974 | Brainin | |
| 3,849,887 A | 11/1974 | Brainin | |
| 3,855,638 A | 12/1974 | Pilliar | |
| 3,934,347 A | 1/1976 | Lash et al. | |
| 4,011,602 A * | 3/1977 | Rybicki et al. | ........... 623/23.76 |
| 4,086,701 A | 5/1978 | Kawahara et al. | |
| 4,180,910 A | 1/1980 | Straumann et al. | |
| 4,185,383 A | 1/1980 | Heimke et al. | |
| 4,186,486 A | 2/1980 | Gordon | |
| 4,199,864 A | 4/1980 | Ashman | |
| 4,215,986 A | 8/1980 | Riess | |
| 4,229,169 A | 10/1980 | Smith et al. | |
| 4,244,689 A | 1/1981 | Ashman | |
| 4,270,905 A | 6/1981 | Mohammed | |
| 4,293,308 A | 10/1981 | Sisti et al. | |
| 4,304,553 A | 12/1981 | Heimke et al. | |
| 4,318,696 A | 3/1982 | Kasama et al. | |
| 4,416,629 A | 11/1983 | Mozsary et al. | |
| 4,437,191 A * | 3/1984 | van der Zel et al. | ...... 623/23.56 |
| 4,530,116 A | 7/1985 | Frey | |
| 4,552,532 A | 11/1985 | Mozsary | |
| 4,575,340 A | 3/1986 | Lustig | |

(Continued)

FOREIGN PATENT DOCUMENTS

DE    2308962    9/1973

(Continued)

*Primary Examiner*—Ralph A Lewis
(74) *Attorney, Agent, or Firm*—Nixon Peabody LLP (57) ABSTRACT

A dental implant and a dental implant assembly comprises a dental implant having a longitudinal-axial-pre-load. The dental implant has an insert portion, and an outer shell portion. The insert portion of the implant is affixed within a longitudinal-axial opening of the outer shell portion of the implant. The affixation of the inner portion within the axial opening of the outer shell portion of the implant applies a pre-load in a longitudinal axial direction on the implant. The dental implant assembly further comprises an abutment and a retaining screw. The abutment is adapted to be attached to the dental implant. The retaining screw is adapted fasten the abutment to the dental implant.

21 Claims, 4 Drawing Sheets

U.S. PATENT DOCUMENTS

| | | | |
|---|---|---|---|
| 4,588,381 A | | 5/1986 | Caracciolo |
| 4,713,003 A | | 12/1987 | Symington et al. |
| 4,713,004 A | | 12/1987 | Linkow et al. |
| 4,716,893 A | | 1/1988 | Fischer et al. |
| 4,722,688 A | | 2/1988 | Lonca |
| 4,818,559 A | | 4/1989 | Hama et al. |
| 4,826,434 A | | 5/1989 | Krueger |
| 4,846,683 A | | 7/1989 | Lazzara et al. |
| 4,850,870 A | | 7/1989 | Lazzara et al. |
| 4,865,603 A | | 9/1989 | Noiles |
| 4,878,914 A | | 11/1989 | Miwa et al. |
| 4,938,693 A | * | 7/1990 | Bulakiev ............... 433/169 |
| 5,000,686 A | | 3/1991 | Lazzara et al. |
| 5,026,280 A | * | 6/1991 | Durr et al. ............ 433/175 |
| 5,026,285 A | * | 6/1991 | Durr et al. ............ 433/173 |
| 5,049,073 A | * | 9/1991 | Lauks ................... 433/173 |
| 5,052,931 A | * | 10/1991 | Kirsch .................. 433/173 |
| 5,125,840 A | * | 6/1992 | Durr et al. ............ 433/173 |
| 5,174,755 A | | 12/1992 | Fukuda |
| 5,188,800 A | | 2/1993 | Green, Jr. et al. |
| 5,205,745 A | | 4/1993 | Kamiya et al. |
| 5,222,983 A | | 6/1993 | Schmitz et al. |
| 5,258,030 A | | 11/1993 | Wolfarth et al. |
| 5,263,986 A | | 11/1993 | Noiles et al. |
| 5,268,001 A | | 12/1993 | Nicholson et al. |
| 5,350,300 A | | 9/1994 | Gallais |
| 5,425,639 A | | 6/1995 | Anders |
| 5,439,381 A | | 8/1995 | Cohen |
| 5,453,007 A | * | 9/1995 | Wagher ................. 433/177 |
| 5,492,470 A | | 2/1996 | Anders |
| 5,527,182 A | | 6/1996 | Willoughby |
| 5,558,517 A | | 9/1996 | Shalaby et al. |
| 5,584,693 A | | 12/1996 | Nishihara |
| 5,607,480 A | | 3/1997 | Beaty |
| 5,759,205 A | | 6/1998 | Valentini |
| 5,766,009 A | | 6/1998 | Jeffcoat |
| 5,782,918 A | | 7/1998 | Klardie et al. |
| 5,833,463 A | * | 11/1998 | Hurson ................. 433/173 |
| 5,873,721 A | | 2/1999 | Willoughby |
| 5,882,351 A | | 3/1999 | Fox |
| 5,931,675 A | | 8/1999 | Callan |
| 5,996,779 A | | 12/1999 | Klardie et al. |
| 6,007,337 A | | 12/1999 | Bauer |
| 6,042,380 A | | 3/2000 | De Rowe |
| 6,083,004 A | | 7/2000 | Misch et al. |
| 6,116,070 A | | 9/2000 | Oshida et al. |
| 6,126,445 A | | 10/2000 | Willoughby |
| 6,142,296 A | | 11/2000 | Klardie et al. |
| 6,152,738 A | | 11/2000 | Aker |
| 6,193,516 B1 | | 2/2001 | Story |
| 6,241,732 B1 | | 6/2001 | Overaker et al. |
| 6,283,753 B1 | | 9/2001 | Willoughby |
| 6,287,116 B2 | * | 9/2001 | Lazzara ................. 433/173 |
| 6,287,310 B1 | | 9/2001 | Fox |
| 6,299,448 B1 | | 10/2001 | Sdrahala et al. |
| 6,431,868 B2 | | 8/2002 | Story |
| 6,840,770 B2 | | 1/2005 | McDevitt |
| 6,863,530 B2 | | 3/2005 | McDevitt |
| 6,991,461 B2 | * | 1/2006 | Gittleman ............. 433/173 |
| 2001/0000486 A1 | | 4/2001 | Story |
| 2003/0124488 A1 | * | 7/2003 | Gittleman ............. 433/173 |

FOREIGN PATENT DOCUMENTS

| | | |
|---|---|---|
| DE | 003531389 | 3/1987 |
| DE | 4019846 | 1/1991 |
| DE | 004321785 | 3/1995 |
| DE | 019705571 | 9/1998 |
| EP | 0213836 | 11/1987 |
| EP | 0409810 | 1/1991 |
| GB | 2176709 | 1/1987 |
| JP | 51-117492 | 10/1976 |
| JP | 51-121998 | 10/1976 |
| JP | 57-75646 | 5/1982 |
| JP | 60-85739 | 5/1985 |
| JP | 60-135042 | 7/1985 |
| JP | 62-172944 | 7/1987 |
| JP | 63-174648 | 7/1988 |
| JP | 1148254 | 6/1989 |
| WO | WO 85/02337 | 6/1985 |
| WO | WO 92/05745 | 4/1992 |
| WO | WO 01/06909 | 2/2001 |
| WO | WO 02/062254 | 8/2002 |

* cited by examiner

PRE-STRESSED IMPLANT COMPONENT AND ASSEMBLY

FIELD OF INVENTION

The present invention relates generally to dental implant systems. More particularly, the present invention relates to dental implant systems wherein an implant is implanted in an edentulous bone of the alveolar arches of the jaws.

BACKGROUND OF THE INVENTION

The use of dental implants to restore missing teeth is becoming increasingly common in dental science. Artificial roots, or implants, are implanted into the bone of patients and used to support replacement teeth. The tooth may be fastened directly to the implants or it may be fastened to an intermediate part called an abutment. In most systems, screws are used to connect the parts.

It will be apparent that when such implanted artificial teeth are used to chew food (mastication), they are subjected to significant forces. These forces place loads on the implant, the abutment, the artificial tooth, as well as the fasteners holding the parts together. A load that is off-axis from a center axis of the implant, abutment, or artificial tooth assembly results in a longitudinal compressive force, a transverse shear force, and a bending moment. Similarly, a lateral load results in a transverse shear force and a bending moment. Prior art dental implants are adapted to resist compressive and transverse shear forces, as well as tensile forces in the case of tensile loading. However, prior art dental implants and dental implant assemblies are unable to withstand higher bending moments without dramatically increasing the risk of structural failure.

Certain prior art implant assemblies secure the abutment to the implant using screws that have a level of screw pre-load to prevent the screw from loosening, such as U.S. Pat. Nos. 6,287,116 and 5,879,161. However, the screw pre-load is placed in the screw to prevent the screw from loosening and the assembly coming apart, not to improve an implants resistance to a bending moment.

For structural analysis purposes, the dental implant assembly may be idealized as a straight rectangular cross-sectioned beam. In a straight beam having either a constant cross-section, or a cross-section gradually changing along the length of the beam, the beam will have a neutral surface defined as a longitudinal surface of zero stress when the beam is subject to pure bending. The neutral surface will contain a neutral axis of every cross-section, such that the neutral axes pass through a centroid of the cross-sections. On one side of the neutral axis, the bending moment will create a compressive force. On the other side of the neutral axis, the bending moment will create a tensile force. A straight beam stress formula is typically called the elastic flexural formula, and the normal stress caused by bending is typically called flexural stress. For example, a beam having a length L, a height H, and a thickness T, will have a stress $\sigma_\Theta$ resulting from a bending moment M based on the following equation:

$$\sigma_\Theta = (M*c)/I$$

where:
$c = H/2$ and
$I = (T*H^3)/12$.

The magnitude of the tensile stress and the compressive stress will be equal when only a bending moment is acting on the beam.

A need exists for an implant assembly that is better able to withstand these flexural stresses such that the structural failure of the implant assemblies is reduced without having to alter the general shape of the implant.

SUMMARY OF THE INVENTION

According to one embodiment of the present invention, a dental implant having a central axis and adapted to be inserted into bone is provided. The dental implant comprises an insert portion, and outer shell portion that has an axial opening. The insert portion is fixed within the axial opening of the outer shell portion. The affixation of the insert portion within the axial opening of the outer shell portion applies a compressive pre-load in the outer shell portion.

According to another embodiment of the present invention, a dental implant assembly having a central axis is provided. The dental implant assembly comprises a dental implant, an abutment, and a retaining screw. The dental implant is adapted to be inserted into bone and has an outer shell portion with a longitudinal-axial-opening and an insert portion. The insert portion of the dental implant is affixed within the longitudinal-axial opening of the outer shell portion. The insert portion is adapted to apply a compressive pre-load on the outer shell portion. The abutment is adapted to engage the insert portion of the dental implant. The retaining screw adapted to fasten the abutment to the dental implant

While the invention is susceptible to various modifications and alternative forms, specific embodiments thereof have been shown by way of example in the drawings and will herein be described in detail. It should be understood, however, that it is not intended to limit the invention to the particular forms disclosed but, on the contrary, the intention is to cover all modifications, equivalents, and alternatives falling within the spirit and scope of the invention as defined by the appended claims.

DESCRIPTION OF ILLUSTRATIVE EMBODIMENTS

Figure 1:
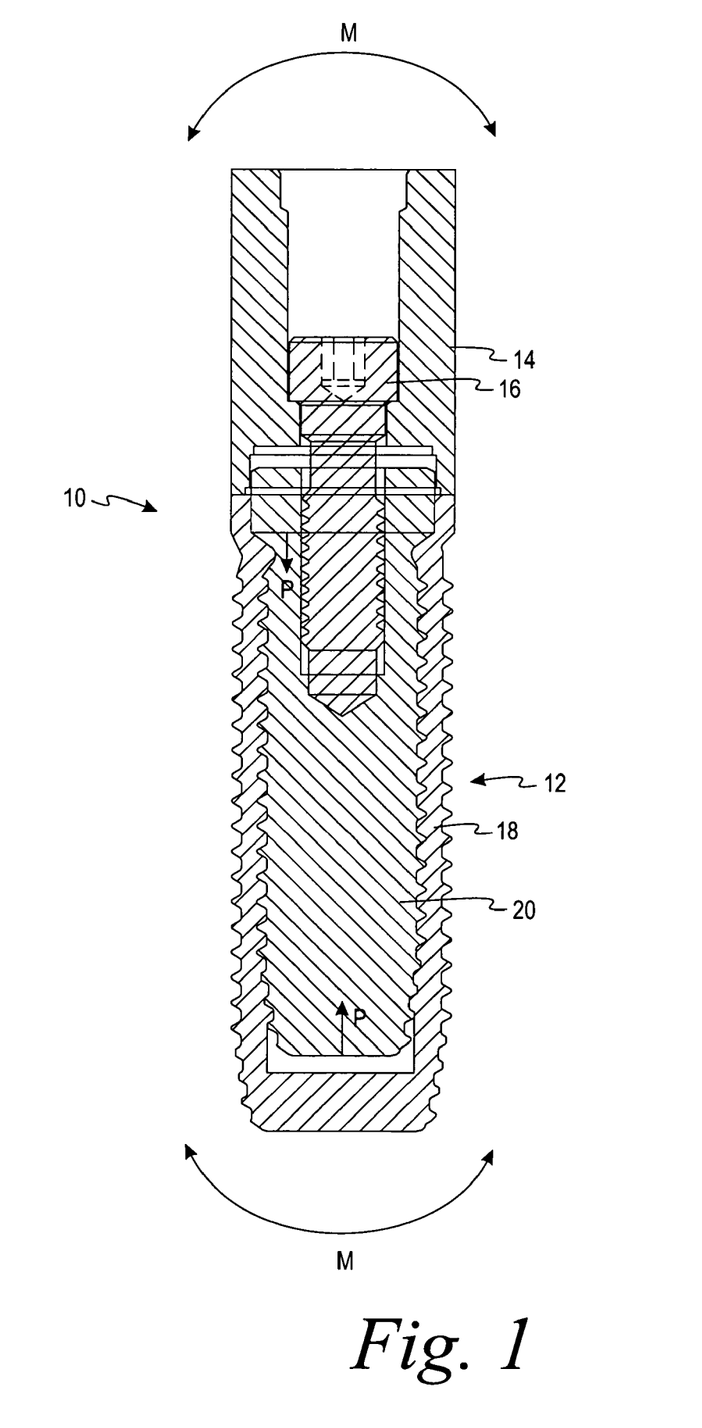
FIG. 1 is a cross-sectional side view of an implant assembly according to one embodiment of the invention.

Referring to FIG. 1, a dental implant assembly 10 comprises an implant 12, an abutment 14, and a retaining screw 16. A central axis passes through the implant assembly 10. The implant 12 further comprises an outer shell portion 18 having an axial opening and an insert portion 20. The insert portion 20 is fixed within the outer shell portion 18 in such a manner as to apply a compressive pre-load to the outer shell portion 18 in a longitudinal-axial direction on the implant 12. Applying a compressive pre-load "P" on the implant 12 reduces the tensile stress within the implant 12 of the implant assembly 10 when an off-axis or lateral occlusal force applied to the implant assembly 10 creates a bending moment "M" in the implant assembly 10.

When the compressive pre-load "P" is applied to the implant 12, the previously mentioned stress formula is modified to account for the pre-load as follows:

$$\sigma_\Theta = (M^*c)/I + P/A;$$

where P is a pre-load and A is a cross-sectional area of the implant 12, and M is the bending moment.

When the pre-load P is a compressive load, the value of P will be a positive value when computing the compressive stress in the implant 12. Thus, the compressive stress created by a bending moment M is increased by the pre-load P. This is because the bending moment M is applying a compressive load to a portion of the implant 12 located on a first side of a neutral axis passing through the implant 12. Similarly, the tensile stress created by the bending moment M is decreased by the pre-load P, as the bending moment M is applying a tensile load to a portion of the implant 12 located on a second side of the neutral axis passing through the implant 12. Thus, the force exerted by the bending moment M on the second side of the neutral axis of the implant 12 is a tensile force, so the pre-load P will help counteract the tensile force exerted by the bending moment M.

The compressive pre-load P causes the neutral axis of the implant 12 to be shifted so that a greater amount of the cross-section of the implant 12 is on the first side of the neutral axis, in compression. Therefore, more of the implant 12 is subjected to compressive forces created by the bending moment M than is subjected to tensile forces created by the bending moment M. Therefore, the implant 12 experiences higher magnitudes of compressive stress than tensile stress when the pre-load P is applied and the bending moment M is applied. Based on the fact that the implant 12 experiences higher compressive stresses compared to tensile stresses, the implant 12 may be made of materials that are more resistive to compressive failures than tensile failures. For example, according to one embodiment of the present invention, the insert portion 20 of the implant 12 is made of a titanium based material, such as commercially pure titanium or a titanium alloy, or another biocompatible material and the outer shell portion 18 of the implant 12 is made of a titanium based material, such as commercially pure titanium or a titanium alloy, a ceramic material, or another biocompatible material. While it is contemplated that the outer shell portion 18 and the insert portion 20 will be made from different materials, the use of the same materials for the outer shell portion 18 and the insert portion 20 will still produce a beneficial effect. Ceramic materials are generally more resistant to failure under compression than they are under tension and are well suited for use in the outer shell portion 18. Therefore, the fact that the pre-load P has caused the implant 12 to have higher values of compressive stress than tensile stress is more than offset by the additional resistance the outer shell portion's material offers to failure under a compressive load, compared to a tensile load. Put another way, the outer shell portion's 18 resistance to compressive failure is much more than the outer shell portion's 18 resistance to tensile failure. Therefore, the fact that the implant 12 experiences greater compressive loading does not increase the likelihood of the implant 12 failing under the stress. The result of the pre-load P in the implant 12 is an implant that offers greater resistance to failure when subjected to a bending moment M created by an off-axis occlusal load.

Figure 2:
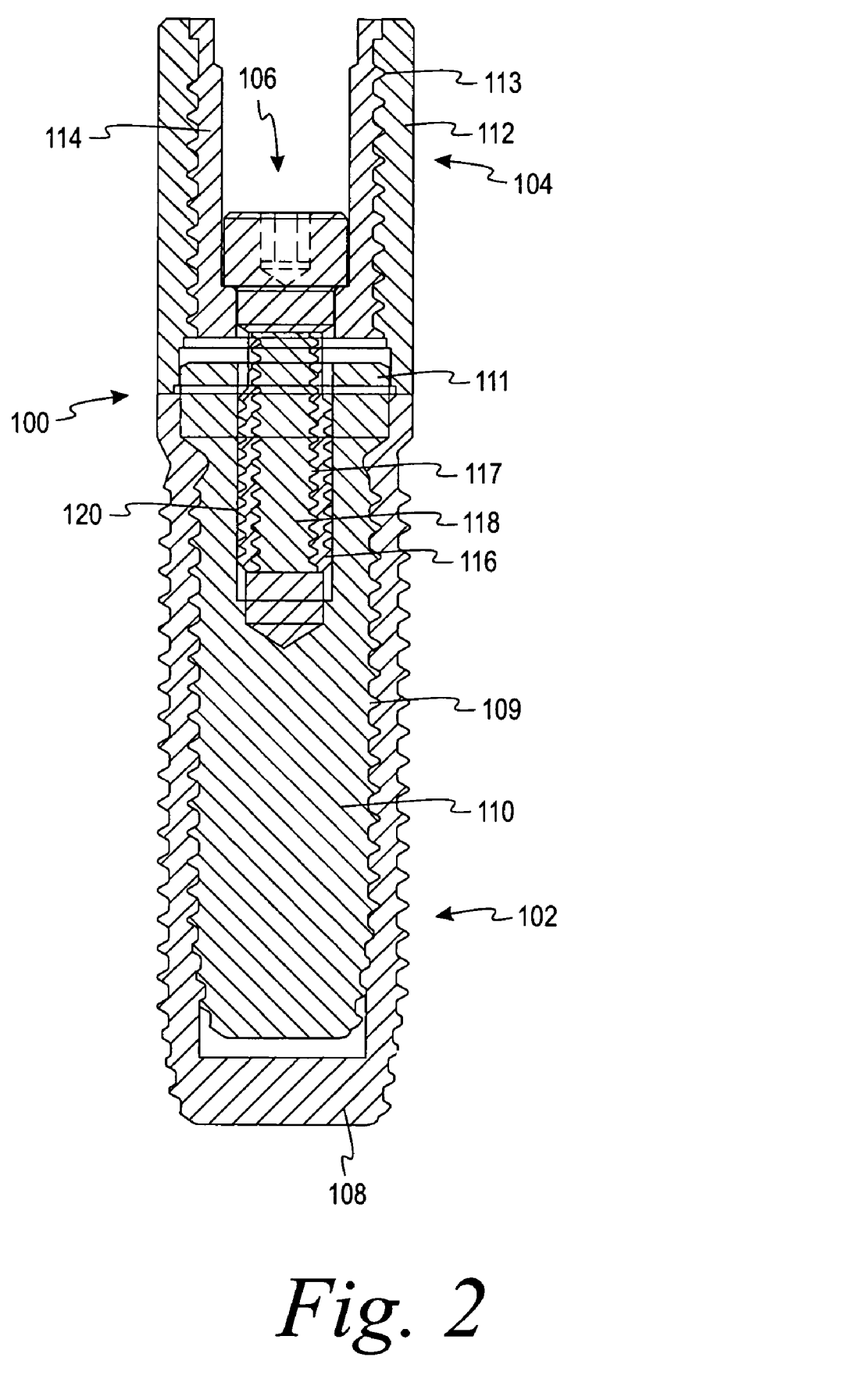
FIG. 2 is a cross-sectional side view of an implant assembly according to another embodiment of the present invention.

While the pre-load P has been described with reference to the implant 12 of the implant assembly 10 of FIG. 1, it is also contemplated to add a similar pre-load to both the abutment, and the retaining screw of the implant assembly. Referring now to FIG. 2, an implant assembly 100 is shown comprising an implant 102, an abutment 104, and a retaining screw 106. As with the implant 12 discussed previously in relation to FIG. 1, the implant 102 has a central axis and comprises an outer shell portion 108 and an insert portion 110. The insert portion 110 of the implant 102 is inserted into the outer shell portion 108 via threads 109. The threads 109 allow the insert portion 110 to be threaded into the outer shell portion 108 of the implant 102, such that a compressive pre-load is present within the outer shell portion 108 of the implant 102. An amount of torque applied to the insert portion 110 while screwing it into the outer shell portion 108 will determine the amount of pre-load within the implant 102. According to one embodiment, the outer shell portion 108 comprises a ceramic material, a titanium based material, or another biocompatible material, and the insert portion 110 comprises a titanium based material, or other biocompatible metal.

According to one embodiment, the implant 102 additionally features a non-rotational feature 111. The non-rotational feature 111 is adapted to position an additional component, such as an abutment, relative to the implant and to prevent the additional component from rotating. The non-rotational feature 111 shown is an external hex located on the insert portion 110 of the implant 102. It is further contemplated that a non-rotational feature may be an internal connector.

Similarly, the abutment 104 may also comprise an outer shell portion or outer shell section 112 and an insert portion or insert section 114. The insert portion 114 of the abutment 104 is inserted into the outer shell portion 112 via threads 113. The threads 113 allow the insert portion 114 to be threaded into the outer shell portion 112 of the abutment 104 such that a compressive pre-load is present within the outer shell portion 112 of the abutment 104. An amount of torque applied to the insert portion 114 while screwing it into the outer shell portion 112 will determine the amount of pre-load within the outer shell portion 112 of the abutment 104. According to one embodiment, the outer shell portion 112 comprises a ceramic material, a titanium based material, or another biocompatible material, and the insert portion 114 comprises a titanium based material, or other biocompatible metal.

The retaining screw 106 may also comprise an outer shell portion or outer segment 116 and an insert portion or insert segment 118 according to the embodiment shown in FIG. 2. The insert portion 118 of the retaining screw 106 is inserted into the outer shell portion 116 via threads 117. The threads 117 allow the insert portion 118 to be threaded into the outer shell portion 116 of the retaining screw 106 such that a compressive pre-load is present within the outer shell portion 116 of the retaining screw 106. An amount of torque applied to the insert portion 118 while screwing it into the outer shell portion 116 will determine the amount of pre-load within the retaining screw 106. According to one embodiment, the outer shell portion 116 comprises a titanium based material or another biocompatible metal, and the insert portion 118 comprises a titanium based material, or other biocompatible metal.

The implant assembly 100 is assembled with the abutment 104 placed on the implant 102 and the abutment 104 is fastened to the implant 102 by the use of the retaining screw 106. The implant 102 further comprises retaining threads 120 that are used in conjunction with the retaining screw 106 in order to assemble the implant assembly 100.

Manufacturing of the implant 102 may be enhanced by threading the insert portion 110 into the outer shell portion 108 via the threads 109 prior to machining the retaining threads 120. The torque applied to the insert portion 110 when inserting the insert portion 110 into the outer shell portion 108 of the implant 102 may cause some distortion of the insert portion 110. Therefore, machining the retaining threads 120 after placing the insert portion 110 into the outer shell portion 108 of the implant 102 reduces the impact of any distortion of the insert portion 110.

Figure 3:
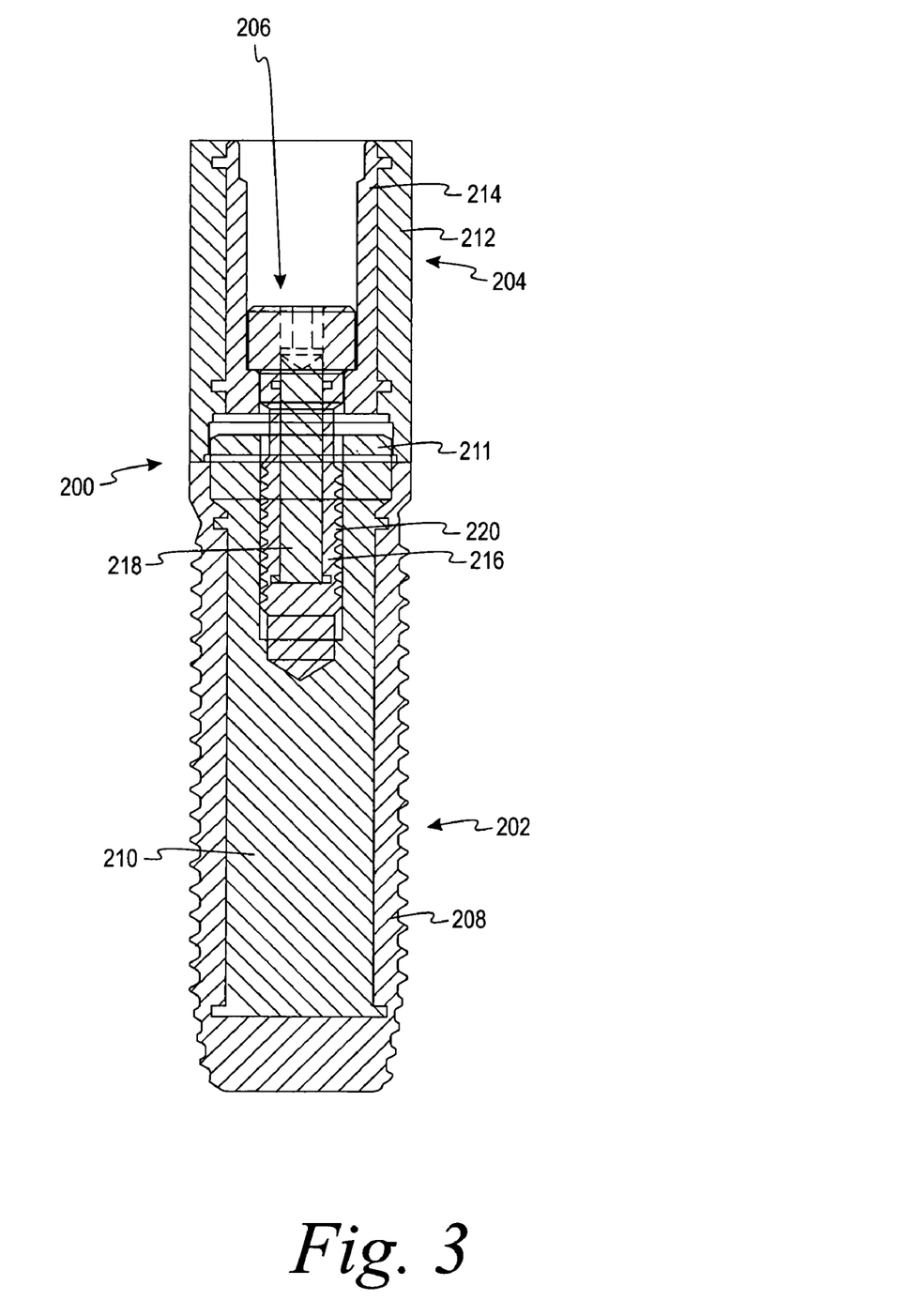
FIG. 3 is a cross-sectional side view of an implant assembly according to a further embodiment of the present invention.

Referring now to FIG. 3, an implant assembly 200 is shown comprising an implant 202, an abutment 204, and a retaining screw 206 according to another embodiment of the present invention. The implant 202 comprises an outer shell portion 208 and an insert portion 210. The insert portion 210 of the implant 202 is inserted into the outer shell portion 208 via a shrink-fit process. The insert portion 210 is manufactured to be slightly smaller than the outer shell portion 208. According to one non-limiting example, the insert portion 210 may be manufactured to be about 98% as large as the outer shell portion 208, although the relative size may vary from that amount. The insert portion 210 would be heated and allowed to expand while the outer shell portion 208 is kept near room temperature. The insert portion 210 would be placed into the outer shell portion 208, and the assembled implant 202 would be allowed to cool. The insert portion 210 would thus be placed within the outer shell portion 208, much like a "spline shaft," and a compressive pre-load would be present within the implant 202. The difference in size between the outer shell portion 208 and the insert portion 210 will determine the amount of pre-load within the implant 202. The greater the size differential, the greater the amount of pre-load. According to one embodiment, the outer shell portion 208 comprises a ceramic material, a titanium based material, or another biocompatible material and the insert portion 210 comprises a titanium based material, or other biocompatible metal.

According to one embodiment, the implant 202 additionally features a non-rotational feature 211. The non-rotational feature 211 is adapted to position an additional component, such as an abutment, relative to the implant and to prevent the additional component from rotating. The non-rotational feature 211 shown is an external hex located on the insert portion 210 of the implant 202. It is further contemplated that a non-rotational feature may be an internal connector.

Similarly, the abutment 204 may also comprise an outer shell portion 212 and an insert portion 214. The insert portion 214 of the abutment 204 is inserted into the outer shell portion 212 via a shrink-fit process, as previously described in relation to the implant 202. The insert portion 214 would thus be placed within the outer shell portion 210 and a compressive pre-load would be present within the abutment 204. The difference in size between the outer shell portion 212 and the insert portion 214 will determine the amount of pre-load within the abutment 204. According to one embodiment, the outer shell portion 212 comprises a ceramic material, a titanium based material, or another biocompatible material, and the insert portion 214 comprises a titanium based material, or other biocompatible metal.

The retaining screw 206 may also comprise an outer shell portion 216 and an insert portion 218 according to the embodiment shown in FIG. 3. The insert portion 218 may also be inserted into the outer shell portion 216 of the retaining screw 206 via a shrink-fit process as previously described in relation to the implant 202. According to one embodiment, the outer shell portion 216 comprises a titanium based material, or another biocompatible metal, and the insert portion 218 comprises a titanium based material, or other biocompatible metal.

The implant assembly 200 is assembled with the abutment 204 fastened to the implant 202 by the use of the retaining screw 206. The implant 202 further comprises retaining threads 220 that are used in conjunction with the retaining screw 206 in order to assemble the implant assembly 200.

Manufacturing of the implant 202 may be enhanced by placing the insert portion 210 into the outer shell portion 208 via the shrink-fit process prior to machining the retaining threads 220. The shrink-fit process used to secure the insert portion 210 into the outer shell portion 208 of the implant 202 may cause some distortion of the insert portion 210. Therefore, machining the retaining threads 220 after placing the insert portion 210 into the outer shell portion 208 of the implant 202 reduces the impact of any distortion of the insert portion 210.

Figure 4:
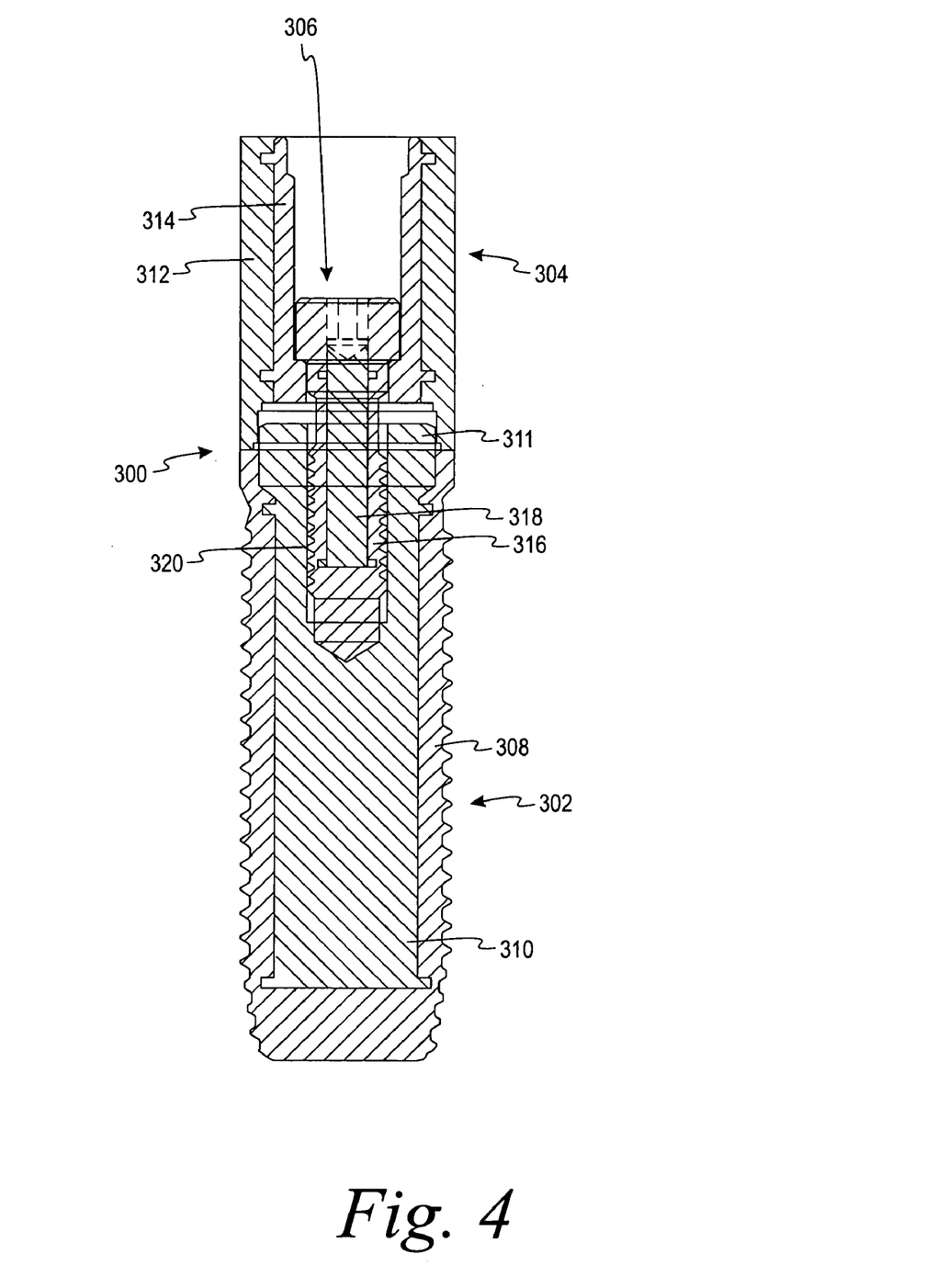
FIG. 4 is a cross-sectional side view of an implant assembly according to yet another embodiment of the present invention.

Turning next to FIG. 4, an implant assembly 300 is depicted comprising an implant 302, an abutment 304, and a retaining screw 306 according to a further embodiment of the present invention. The implant 302 comprises an outer shell portion 308 and an insert portion 310. The insert portion 310 of the implant 302 is inserted into and retained within the outer shell portion 308 via a shape-memory-alloy process. The insert portion 310 is manufactured from a shape-memory alloy. It is contemplated that the shape-memory allow insert portion 310 is machined so that it is undersized compared to the outer shell portion. According to one embodiment the insert portion 310 is from about 95% to about 99.5% the size of an opening in the outer shell portion 308. The insert portion 310 is then cooled so that it transforms from the austenitic phase to the martensitic phase. While in the martensitic phase, the insert portion is subjected to a force along its longitudinal axis and stretched so that the length of the insert portion 310 is about the same as the length of an opening in the outer shell portion 308. The insert portion 310 is placed within the outer shell portion 308 of the implant 302 while still in the martensitic state. The insert portion 302 may have a "spline shaft" shape in order to secure the insert portion within the outer shell portion. The implant 302 is then heated above an austenitic transition temperature of the shape-memory alloy of the insert portion 310, causing the insert portion 310 to attempt to shrink back to an undersized state relative to the outer shell portion 308, placing a compressive stress on the outer shell portion 308. As the insert portion 310 shrinks along its longitudinal axis, a compressive pre-load is left within the outer shell 308 of the implant 302. The amount of pre-load within the implant 302 is based upon the amount of deformation of the insert portion 310 while the shape-memory alloy is in the martensitic state. According to one embodiment, the outer shell portion 308 comprises a ceramic material, a titanium based material, or another biocompatible material and the insert portion 310 comprises a shape-memory-alloy such as Nickel-Titanium (NiTi).

According to one embodiment, the implant 302 additionally features a non-rotational feature 311. The non-rotational feature 311 is adapted to position an additional component, such as an abutment, relative to the implant and to prevent the additional component from rotating. The non-rotational feature 311 shown is an external hex located on the insert portion 310 of the implant 302. It is further contemplated that a non-rotational feature may be an internal connector.

Similarly, the abutment 304 may also comprise an outer shell portion 312 and an insert portion 314. The insert portion 314 of the abutment 304 is inserted into the outer shell portion 312 via a shape-memory-alloy process, as previously described in relation to the implant 302. The insert portion 314 would thus be placed within the outer shell portion 312 and a compressive pre-load would be present within the abutment 304. The amount of pre-load within the abutment 304 is based upon the amount of deformation of the insert portion 314 while the shape-memory alloy is in the martensitic state. According to one embodiment, the outer shell portion 312 comprises a ceramic material, a titanium based material, or another biocompatible material, and the insert portion 314 comprises a shape-memory alloy such as NiTi.

The retaining screw 306 may also comprise an outer shell portion 316 and an insert portion 318 according to the embodiment shown in FIG. 4. The insert portion 318 may also be inserted into the outer shell portion 316 of the retaining screw 306 via a shape-memory-alloy process as previously described in relation to the implant 302. According to one embodiment, the outer shell portion 316 comprises a titanium based material, or another biocompatible metal, and the insert portion 318 comprises a shape-memory-alloy such as NiTi.

The implant assembly 300 is assembled with the abutment 304 fastened to the implant 302 by the use of the retaining screw 306. The implant 302 further comprises retaining threads 320 that are used in conjunction with the retaining screw 306 in order to assemble the implant assembly 300.

Manufacturing of the implant 302 may be enhanced by placing the insert portion 310 into the outer shell portion 308 via the shape-memory-alloy process prior to machining the retaining threads 320. The shape-memory-alloy process used to secure the insert portion 310 into the outer shell portion 308 of the implant 302 may cause some distortion of the insert portion 310. Therefore, machining the retaining threads 320 after placing the insert portion 310 into the outer shell portion 308 of the implant 302 reduces the impact of any distortion of the insert portion 310.

According to another embodiment of the present invention, the outer shell material is high compressive strength material such as a ceramic like TTZ Zirconia. The insert portion material is a high tensile strength material such as a metal alloy like Ti-6Al-4V alloy. The combination of a high compressive strength outer shell and a high tensile strength insert portion provides greater resistance to structural failure than a single material implant, abutment, or screw.

While various embodiments of a dental implant assembly have been described wherein the insert portion of a set of components, i.e., an implant, an abutment, and a retaining screw, have been manufactured using the same process, it is contemplated that the components may be manufactured using a combination of manufacturing methods. For example, an implant with a pre-load may be manufactured by threading an insert portion into an outer shell portion, an abutment with a pre-load may be manufactured by using a shrink-fit process, and a retaining screw having a pre-load may be manufactured using a shape-memory-alloy process. It is contemplated that any combination of manufacturing methods may be used.

Additionally, it is also contemplated that threads of a retaining screw having a pre-load be machined following the insertion of the insert portion into the outer shell portion of the retaining screw, as the insertion may distort the insert portion.

It is further contemplated that a through-bore of an abutment having a pre-load be machined following the insertion of the insert portion into the outer shell portion of the abutment, as the insertion may distort the insert portion.

According to yet another embodiment of the present invention, the abutments 104, 204, 304 described in relation to FIGS. 2-4 may be used with a prior art dental implant and retaining screw where the dental implant and retaining screw do not feature insert portions and outer shell portions. In this way the strength of an implant assembly is increased by the additional resistance to a bending moment the pre-stressed abutment provides.

According to still a further embodiment of the present invention, the retaining screws 106, 206, 306 described in relation to FIGS. 2-4 may be used with a prior art dental implant and abutment where the dental implant and abutment do not feature insert portions and outer shell portions. In this way the strength of an implant assembly is increased by the additional resistance to a bending moment the pre-stressed retaining screw provides.

While particular embodiments and applications of the present invention have been illustrated and described, it is to be understood that the invention is not limited to the precise construction and compositions disclosed herein and that various modifications, changes, and variations may be apparent from the foregoing descriptions without departing from the spirit and scope of the invention as defined in the appended claims.

What is claimed is:

1. A dental implant having a central axis and configured to be inserted into bone comprising:
   a solid outer shell portion having a first closed end and a second, opposite end having an axial opening therethrough, the axial opening of the outer shell portion having a threaded surface; and
   an insert portion configured to receive a screw to hold an abutment to the outer shell portion, the insert portion having a threaded outer surface, the threaded outer surface having a single unitary thread extending along its length, the insert portion further comprising a non-rotational structure to assist in preventing an additional component from rotating relative to the implant, a material forming the outer shell portion having a greater compressive strength than a material forming the insert portion, the material forming the insert portion having a greater tensile strength than the material forming the outer shell portion,
   wherein the insert portion is affixed within the axial opening of the outer shell portion, and the affixation of the insert portion within the axial opening of the outer shell portion is configured to apply a compressive pre-load in the outer shell portion.

2. The dental implant of claim 1, wherein the insert portion is affixed within the outer shell portion by threading the insert portion into the outer shell portion.

3. The dental implant of claim 1, wherein the insert portion comprises a metal material.

4. The dental implant of claim 1, wherein the non-rotational structure is an external hex.

5. The dental implant of claim 1, wherein the non-rotational structure is an internal hex.

6. The dental implant assembly of claim 1, wherein outer shell portion comprises a ceramic material.

7. The dental implant assembly of claim 6, wherein the insert portion comprises a titanium based material.

8. The dental implant of claim 1 further comprising an abutment, wherein the abutment is the additional component positioned relative to the implant by the non-rotational structure.

9. A dental implant assembly having a central axis comprising:
   a dental implant configured to be inserted into bone having an outer shell portion having a longitudinal-axial opening and an insert portion, the insert portion being affixed within the longitudinal-axial opening of the outer shell portion, such that the insert portion is configured to apply a compressive pre-load on the outer shell portion;
   an abutment configured to engage the insert portion of the dental implant; and
   a retaining screw configured to fasten the abutment to the insert portion,
   wherein at least one of the abutment and retaining screw includes an outer shell section and an insert section affixed within a longitudinal-axial opening of the outer shell section by threading the insert section into the outer shell section, the affixation of the insert section within the outer shell section being configured to apply a compressive pre-load on the outer shell section, a material forming the outer shell portion having a greater compressive strength than a material forming the insert portion, the material forming the insert portion having a greater tensile strength than the material forming the outer shell portion.

10. The dental implant assembly of claim 9, wherein the dental implant outer shell portion comprises a ceramic material.

11. The dental implant assembly of claim 9, wherein the dental implant insert portion comprises a titanium based material.

12. The dental implant assembly of claim 9, wherein the insert portion of the dental implant has a threaded outer circumferential surface and the axial opening of the outer shell portion of the dental implant has an inner threaded surface and the insert portion of the implant is affixed within the outer shell portion of the implant by threading the insert portion into the outer shell portion of the implant.

13. The dental implant assembly of claim 9, wherein the insert portion of the implant is affixed within the axial opening of the outer shell portion of the implant by a shrink-fit process.

14. The dental implant assembly of claim 9, wherein the insert portion of the dental implant is affixed within the axial opening of the outer shell portion of the implant by a shape-memory-alloy process.

15. The dental implant assembly of claim 9, wherein the abutment includes the outer shell section and the insert section.

16. The dental implant assembly of claim 15, wherein the abutment outer shell section comprises a ceramic material.

17. The dental implant assembly of claim 15, wherein the abutment insert section comprises a titanium based material.

18. The dental implant assembly of claim 15, wherein the insert section of the abutment has a threaded outer circumferential surface and the axial opening of the outer shell section of the abutment has a threaded surface.

19. The dental implant assembly of claim 9, wherein the retaining screw includes the outer section and the insert section.

20. The dental implant assembly of claim 19, wherein the insert section of the retaining screw has a threaded outer circumferential surface and the axial opening of the outer section of the retaining screw has a threaded surface.

21. A dental implant assembly comprising:
a dental implant configured to be inserted into bone;
an abutment; and
a retaining screw configured to fasten the abutment to the dental implant,
wherein at least one of the abutment and retaining screw includes an outer shell section and an insert section threaded within a longitudinal-axial opening of the outer shell section, the insert section being surrounded by the outer shell section, the affixation of the insert section within the outer shell section being configured to apply a compressive pre-load on the outer shell section, a material forming the outer shell section having a greater compressive strength than a material forming the insert section, the material forming the insert section having a greater tensile strength than the material forming the outer shell section.

* * * * *